US008529457B2

(12) United States Patent
Devot et al.

(10) Patent No.: US 8,529,457 B2
(45) Date of Patent: Sep. 10, 2013

(54) SYSTEM AND KIT FOR STRESS AND RELAXATION MANAGEMENT

(75) Inventors: Sandrine Magali Laure Devot, Aachen (DE); Andreas Brauers, Aachen (DE); Elke Naujokat, Aachen (DE); Robert Pinter, Aachen (DE); Harald Reiter, Aachen (DE); Jeroen Adrianus Johannes Thijs, Waldfeucht (DE)

(73) Assignee: Koninklijke Philips N.V., Eindhoven (NL)

( * ) Notice: Subject to any disclaimer, the term of this patent is extended or adjusted under 35 U.S.C. 154(b) by 386 days.

(21) Appl. No.: 12/918,531

(22) PCT Filed: Feb. 16, 2009

(86) PCT No.: PCT/IB2009/050628
§ 371 (c)(1),
(2), (4) Date: Aug. 20, 2010

(87) PCT Pub. No.: WO2009/104127
PCT Pub. Date: Aug. 27, 2009

(65) Prior Publication Data
US 2010/0324427 A1    Dec. 23, 2010

(30) Foreign Application Priority Data

Feb. 22, 2008    (EP) ..................... 08151805

(51) Int. Cl.
*A61B 5/00*    (2006.01)
*A61B 5/02*    (2006.01)
*A61B 5/04*    (2006.01)
*A61B 5/08*    (2006.01)

(52) U.S. Cl.
USPC .......... 600/484; 600/300; 600/301; 600/481; 600/508; 600/520; 600/529; 600/536

(58) Field of Classification Search
USPC ................. 600/301, 484, 520, 529–543, 300, 600/481, 508
See application file for complete search history.

(56) References Cited

U.S. PATENT DOCUMENTS 5,304,112 A * 4/1994 Mrklas et al. ................... 600/27
(Continued)

FOREIGN PATENT DOCUMENTS

| WO | 9620639 A1 | 7/1996 |
|---|---|---|
| WO | 2005044092 A2 | 5/2005 |

OTHER PUBLICATIONS

Lucini et al: "Impact of Chronic Psychosocial Stress on Autonomic Cardiovascular Regulation in Otherwise Healthy Subjects"; Hypertension, vol. 46, 2005, pp. 1201-1206.
(Continued)

*Primary Examiner* — Patricia Mallari
*Assistant Examiner* — Puya Agahi

(57) ABSTRACT

This invention relates to a system and a kit for stress and relaxation management. A cardiac activity sensor (101) is used for measuring the heart rate variability (HRV) signal of the user and a respiration sensor (102) for measuring the respiratory signal of the user. The system contains a user interaction device (103) having an input unit (104) for receiving user specific data and an output unit for providing information output to the user. A processor (106) is used to assess the stress level of the user by determining a user related stress index. The processor is also used to monitor the user during a relaxation exercise by means of determining a relaxation index based on the measured HRV and respiratory signals, the relaxation index being continuously adapted to the incoming measured signals and based thereon the processor instructs the output unit to provide the user with biofeedback and support messages. Finally, the processor uses the user specific data as an input in generating a first set of rules defining an improvement plan for self-management of stress and relaxation. The first set of rules is adapted to trigger commands instructing the output unit to provide the user with motivation related messages. Also, at least a portion of said user specific data is further used to define a second set of rules indicating the user's personal goals.

17 Claims, 5 Drawing Sheets

(56) References Cited

U.S. PATENT DOCUMENTS

| | | | | |
|---|---|---|---|---|
| 5,993,401 | A * | 11/1999 | Inbe et al. | 601/46 |
| 6,493,578 | B1 * | 12/2002 | DeFeo | 600/546 |
| 6,607,484 | B2 * | 8/2003 | Suzuki et al. | 600/300 |
| 2002/0083122 | A1 | 6/2002 | Lemchen | |
| 2003/0130595 | A1 | 7/2003 | Mault | |
| 2003/0204412 | A1 * | 10/2003 | Brier | 705/2 |
| 2004/0267565 | A1 | 12/2004 | Grube | |
| 2005/0096555 | A1 | 5/2005 | Elliott | |
| 2005/0154264 | A1 | 7/2005 | Lecompte et al. | |
| 2005/0256414 | A1 * | 11/2005 | Kettunen et al. | 600/509 |
| 2005/0288601 | A1 * | 12/2005 | Wood et al. | 600/513 |
| 2007/0056594 | A1 * | 3/2007 | El-Nokaly et al. | 128/897 |
| 2008/0071137 | A1 * | 3/2008 | Schachter et al. | 600/27 |
| 2008/0171914 | A1 * | 7/2008 | Ouwerkerk et al. | 600/300 |
| 2008/0214944 | A1 * | 9/2008 | Morris et al. | 600/509 |
| 2009/0005657 | A1 * | 1/2009 | Bodlaender et al. | 600/301 |
| 2009/0082685 | A1 * | 3/2009 | Stabler et al. | 600/523 |
| 2009/0192402 | A1 * | 7/2009 | Corn | 600/534 |

OTHER PUBLICATIONS

Grossman et al: "Breathing-Control Lowers Blood Pressure"; Journal of Human Hypertension; (2001), vol. 15, pp. 263-269.

Shusterman et al: "Sympathetic Nervous System Activity in Stress and Biofeedback Relaxation"; IEEE Engineering in Medicine and Biology Magazine, Mar./Apr. 2005, pp. 52-57.

Schein et al: "Treating Hypertension With a Device That Slows and Regularises Breathing: A Randomised, Double-Blind Controlled Study"; Journal of Human Hypertension, (2001), vol. 15, pp. 271-278.

Paajanen et al; "Electromechanical Film (EMFi)—A New Multipurpose Electret Material"; Sensors and Actuators, (2000), vol. 84, pp. 95-102.

Gordon et al: "Getting Risk Factors to Goal: Lifestyle Intervention Is Worth Thhe Effort in Patients With Hypertension, Hyperlipidemia, and/or Hyperglycemia"; Paper Presented at the 53rd Annual Scientific Sessions of the American College of Cardiology, Mar. 7-10, 2004, New Orleans, LA.

The Handbook of Motivation and Cognition: Foundations of Social Behavior, vol. 2, E. Tory Higgins and Richard M. Sorrentino, Editors, Chapter 2, Author Gollwitzer, "Action Phases and Mindsets"; pp. 53-92.

Malik et al: "Heart Rate Variability: Standards of Measurement, Physiological Interpretation, and Clinical Use"; European Heart Journal (1996), vol. 17, pp. 354-381.

* cited by examiner

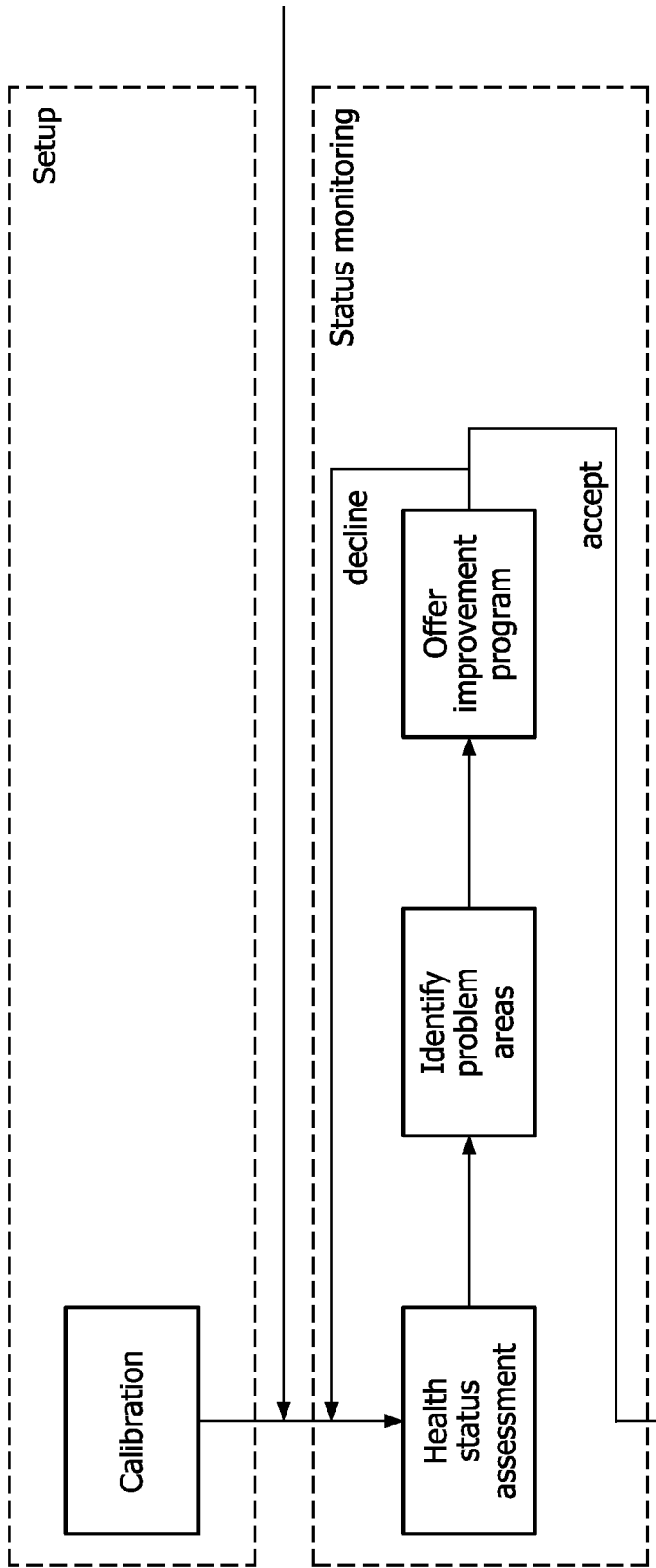

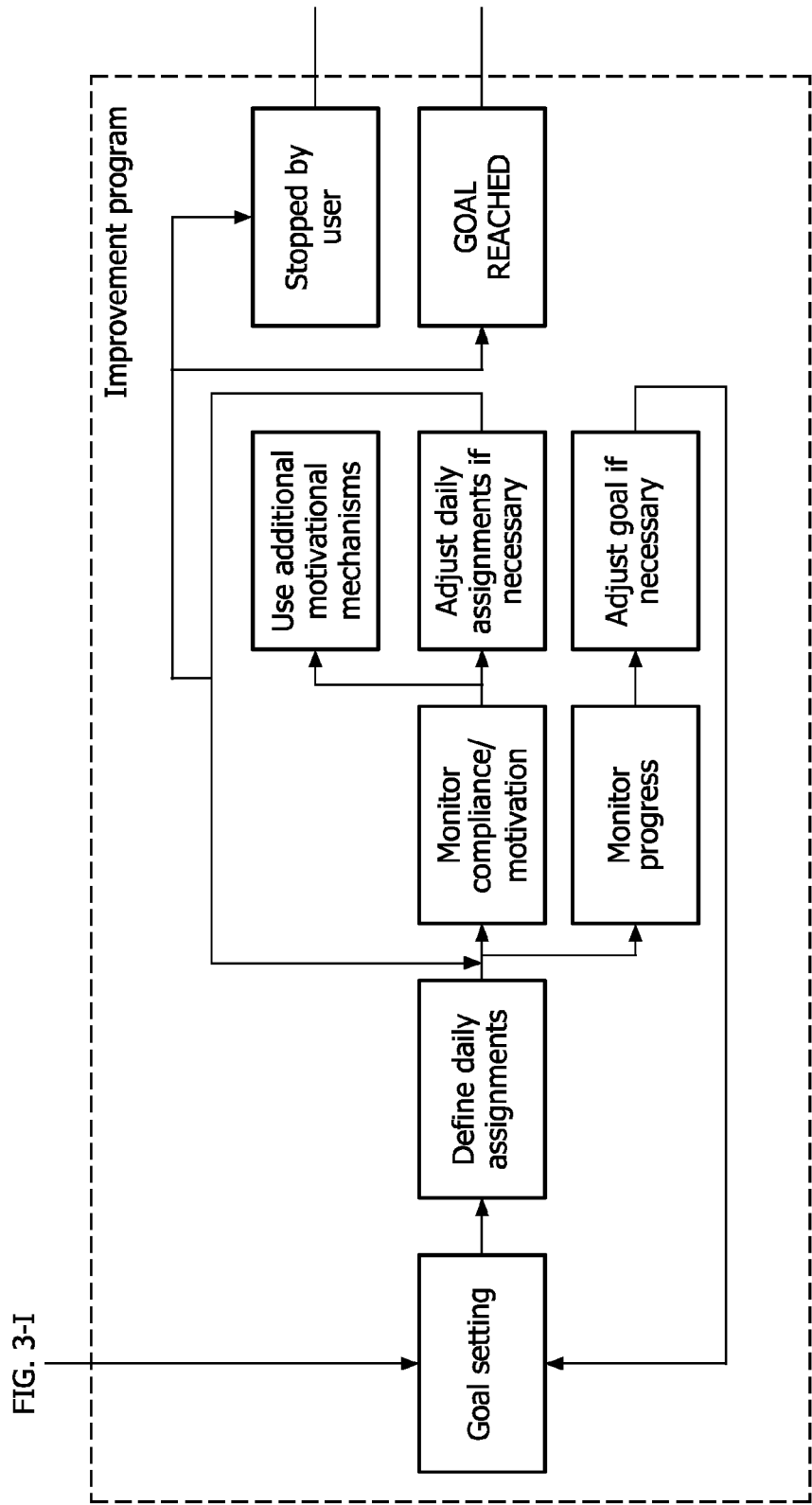
FIG. 3-II

US 8,529,457 B2

SYSTEM AND KIT FOR STRESS AND RELAXATION MANAGEMENT

FIELD OF THE INVENTION

The present invention relates to a system and a method for stress and relaxation management.

BACKGROUND OF THE INVENTION

Stress has become a social issue because of its growing deleterious effect on performance, quality of life and health. Some attempts have been done to define stress indexes, but are more related to stress reactivity and recovery, e.g. during specific relaxation exercises and not to a real-life level. Several stress management devices have been developed that rely on the measurement of at least one vital parameter and give feedback to the user about changes of that parameter or a stress index into which it is translated. The procedure is called biofeedback. By observing the direct feedback, the user can learn to control his bodily functions in a way that is favorable in some context. Biofeedback devices for stress management employ measurements of various vital parameters that can easily be measured, like ECG, skin temperature, skin conductivity (galvanic skin response) and heart rate (often a finger- or ear-clip containing an optical heart rate measurement). The idea is in any case that by displaying the measurement results or some kind of index into which the measurement results are translated, the user learns to control his bodily functions such that he gets into a more relaxed state. However, the overall stress level is difficult to assess and is characterized by a pronounced variability between subjects. Stress also depends largely on the individual perception, which can vary from day to day. That is why the proposed stress index depends on several parameters, including outputs of a questionnaire and a measurement protocol.

Most of the stress management devices are limited to monitoring a single parameter. For example, assessment of the user's condition and instructions for relaxation exercise are only based on the measured HRV. Besides heart rate variability, other physiological parameters have shown to be related to the level of stress/relaxation, such as the respiration (rate and volume/amplitude). The users of these devices are left to themselves to find motivation, to implement the plans for achieving their targets, to monitor progress and to find and suggest solutions when problems arise. However, traditional practitioners do not have the time, the infrastructure, the resources, the training, and reimbursement possibilities to address the needs of those people.

BRIEF DESCRIPTION OF THE INVENTION

The object of the present invention is to overcome the above mentioned drawbacks by providing a system and a method that assesses the user's stress level and assists him or her in reducing the stress level.

According to one aspect the present invention relates to system for stress and relaxation management, comprising:

at least one cardiac activity sensor for measuring a heart rate variability (HRV) signal of a user, at least one respiration sensor for measuring a respiratory signal of the user, a user interaction device comprising an input unit for receiving user specific data and an output unit for providing information output to the user, and a processor adapted to assess the stress level of the user by determining a user related stress index, the stress index being used as an input in triggering commands instructing the output unit to provide the user with a messages indicating the stress level of the user, the processor further being adapted to monitor the user during a relaxation exercise by means of determining a relaxation index based on the measured HRV and respiratory signals by means of calculating an index of coherence between the HRV signal and the respiratory signal during the relaxation exercise, the relaxation index being continuously adapted to the incoming measured signals and based thereon the processor instructs the output unit to provide the user with biofeedback and support messages, the processor further being adapted to use the user specific data as an input in generating a first set of rules defining an improvement plan for self-management of stress and relaxation, said first set of rules being adapted to trigger commands instructing the output unit to provide the user with motivation related messages.

Accordingly, a system is provided for improving the physiological state of the user. The motivation related messages may be provided to the user e.g. on daily basis and may relate to stress/relaxation scores and suggestions to reduce the stress level and perform a relaxation exercises. Thus, the user can monitor whether the relaxation exercise is successful or not and when a sufficient relaxation level is reached. Put in other words, the user can monitor how successful his or her efforts are to adopt a healthier lifestyle. The input unit may be presented to the user on e.g. a display where various questionnaires are presented to the user. Accordingly, the system can be customized to the user, who can enter data e.g. relating to age, gender, smoking habits, blood pressure and the like. Additional input data may e.g. be whether the user has previously been stressed or has had heart attack or nervous breakdown etc. Thus, the system is customized to the user and is capable to take these various input data into account when e.g. making a training program for the user.

In one embodiment, said user specific data comprises:
input data entered by the user via said input unit,
input data obtained from the user via a response to questionnaires presented to the user,
input data from an external agent communicating via said input unit,
data obtained from measured signals from said sensors, and
a combination of one or more of the above.

The data obtained from the measured signals may be over a pre-fixed period, e.g. 1 week. After the initialization phase, the user specific data typically also comprises all measured data in the past and not only that obtained during this initialization phase.

In one embodiment, at least a portion of said user specific data is further used to define a second set of rules indicating the user's personal goals.

Accordingly, said goals may be set according to the individual preferences of the user. For example goals may be oriented towards improved performance or oriented towards changes in behavior.

The data from the questionnaires may thus be used to define the personalized set of goals in addition to the baseline data measured during the pre-fixed time period, which could be called the "initialization phase", of duration of e.g. 1 week.

In one embodiment, the processor is further adapted to assess the stress level of the user by determining a user related stress index based on the HRV signal in combination with the received user specific data, the user related stress index being determined based on a first and a second HRV parameter value associated to a first and a second posture, where the difference between HRV parameter values is used as an indicator to determine the user related stress index.

The system will thus be able to determine a personalized stress index. Stress assessment is based on heart rate variability (HRV), where the measurement procedure consists typically of a simple protocol where in the first posture the user rests for a few minutes and in the second posture the user stands. During the protocol, a few HRV parameters in frequency domain will be derived. It has been namely observed during active standing—a stimulus that physiologically enhances sympathetic activity—that a significantly smaller increase of the normalized Low Frequency (LF) component and a significantly smaller reduction of the normalized High Frequency (HF) component occur in stressed patients compared to control ones. Such changes suggest a reduced responsiveness to excitatory stimuli during stress.

In one embodiment, said processor is further adapted to compare the user related stress index, initially with baseline measures and subsequently with the previous determined stress indexes, wherein said comparing results in triggering commands instructing the output unit to provide the user with messages indicating the stress level of the user and trends.

In one embodiment, said baseline measures are determined during an initialization phase where the processor uses the measured signals to determine one or more of the following parameters:

a personal range for the stress index value, determined from said stress assessment, a personal range for the relaxation index value determined from said relaxation exercise, parameters which can be extracted from the cardiac activity and respiratory sensors, including one or more of the following:

HRV parameters, breathing rate parameter, breathing amplitude parameter.

As an example, the initialization phase may last for one week, where during this week cardiac activity and respiratory signals are measured. Some of the sensors may be integrated in the user's bed so as to monitor the user during the nights. The user may also be asked to perform the stress assessment and the relaxation exercises, but the user could decide to do it several times. From these measurements, typical values for the stress/relaxation indexes and for the vital signs are derived. Moreover, the user may have to answer several questionnaires to retrieve user's general information, subjective stress assessment (stress perception) and user's preferences. Based on the data obtained during the week, said baseline measures are provided.

Considering the stress index in further details, from the subjective stress assessment, one can deduce a stress score. From the stress assessment measures, at least one stress index is obtained. With both values, the system is able to generate a recommendation with respect to the stress level the user could achieve in the near future, following said improvement plan. This goal in terms of the stress index should represent for the user an improvement (more relaxed state), but also be feasible. To make the recommendation, the system may also use other information coming from the baseline measures, such as the stress profile during the week, the performance the user showed during the relaxation exercise, etc. The analysis could lead to a recommendation, which is more ambitious or not for the user.

In one embodiment, said user specific data comprises:

input data entered by the user via said input unit, input data obtained from the user via a response to questionnaires presented to the user, input data from an external agent communicating via said input unit, data obtained from measured signals from said sensors, and a combination of one or more of the above, wherein said comparing with the previous determined stress indexes further includes comparing the stress index with the second set of rules indicating the user's personal goals and adapting the second set of rules to the outcome of the comparing with the second set of rules.

Continuing with said example, after several weeks of use, the system may be able to compare the current stress index achieved by the user with his goal, i.e. the desired stress index. If the user reached his goal, the system may recommend the user to modify the goal to a more ambitious level and may compliment the user. If the user has not reached his goal, but is not so far, the system may encourage the user to continue his efforts and give some individualized support messages. If the user is far away from his goal, the system may suggest to set a less ambitious goal, to propose other tips and relaxation exercises (such as yoga and other standard relaxation techniques) to help further the user.

In one embodiment, the processor is further adapted to determine at least one of the following parameters:

trend and progress related parameter indicating trends and progress of the user, where the determining is based on one or more of the following:

comparing said indexes with previous indexes, comparing said indexes with said second set of rules comparing said indexes with previous indexes and said second set of rules performance related parameter indicating the performance of the user during the relaxation exercise, said determining being based on comparing the determined relaxation index with the previous ones, and compliance related parameter indicating the compliance of the user to follow said second set of rules, said determining being based on the monitoring of determined indexes and said current set of second set of rules, wherein the processor is further adapted to adapt the first set of rules to one or more of said parameters.

Accordingly, the current stress index is compared with the previous values of the stress index, and the performance related parameter of the relaxation exercise is compared with the previous values obtained in previous relaxation exercises. It should be noted that the relaxation index varies continuously during the relaxation exercise, so that there is no unique value per relaxation exercise, but many of them. Thus, one needs to define a related parameter summarizing the performance of the exercise. This could be the last value of the relaxation index obtained during the relaxation exercise, or the mean value of all relaxation indexes during the relaxation exercise, etc. By the term comparing said indexes with said second set of rules is preferably meant that objective measurements via the indexes are compared to goals set by the user. Moreover, objective measurements are also compared to subjective assessment of stress via said questionnaires. The compliance is typically determined by looking at said questionnaires and the measurements. The measurements indicate whether the user has performed the exercises or not (these could be the stress assessment, the relaxation exercises, etc.), how often and how long he has performed. This allows evaluating if the user followed correctly his plans or not. For compliance, there is no comparison with previous indexes, but just the monitoring of when, how long and how often the user has done something. This is then compared to said improvement plan, which is adapted if the compliance is too low.

In one embodiment, prior to defining said second set of rules, proposal rules are presented to the user via said output unit, where in case the user agrees on the proposal rules via said input unit, said processor issues a command triggering said proposal rules to become said second set of rules.

Therefore, a user friendly way is provided allowing the user to select pre-set rules, so that the user does not have to manually define the second set of rules.

In one embodiment, the second set of rules is used as input in defining said first set of rules.

The user goals are accordingly used as input in the comparison between the current stress indexes obtained by the user and what he set in his goals. Thus, it may be determined if the user has reached his objectives, or not, and how far he is. This is preferably then used to adapt the improvement plan, e.g. proposal rules for goal settings are modified, e.g. specific coaching is set up, etc.

In one embodiment, said comparing of the user related stress index with the baseline measures and subsequently with the previous determined stress indexes further includes means of comparing the subsequent stress indexes with the previous determined stress indexes along with said second set of rules indicating the user's personal goals.

Thus, the user's personal goals are incorporated into said comparison.

In one embodiment, the at least one cardiac activity and respiration sensors are wireless and unobtrusive.

By the term unobtrusive is meant that the dimension of the sensors is such that they are comfortable and do not disturb the user's life.

In one embodiment, said at least one cardiac activity and respiration sensors are integrated into textiles.

Accordingly, the user can carry the sensors without noticing it.

In one embodiment, the system further comprises
a temperature sensor adapted to measure the temperature of the skin of the user,
a galvanic skin response sensor adapted to measure the galvanic skin response,
a pillow electrode integrated into a pillow combined with a foot mat electrode integrated into a bed sheet for measuring heart rate (HR) and HRV signals,
a bed post sensor adapted to be integrated or mounted to a bed frame and measuring HR or HRV or both HR and HRV signals,
a slat sensor or a foil sensor adapted to be integrated into a bed or a sofa or a chair for measuring at least one of the following:
HR signal,
HRV signal,
the respiration of the user,
the activity of the user
a combination of one or more of said sensors.

In one embodiment, the processor is an external processor comprised in an external computer system or in a hand-held device, the system further comprising a transceiver for transmitting the measured signals to the external computer system or the hand-held device where said processing steps are performed.

Accordingly, since the processing power is located externally the intelligence of the system does not have to be very high, which can lead to a reduced cost of the system and thus an economical benefit for the user purchasing the system.

In one embodiment, the system further comprises a transceiver, the processor, the user interaction device and the transceiver being integrated into a hand-held device.

In one embodiment, the first posture of said stress assessment is a rest posture and the second posture is a stand-up posture or any posture change resulting in a new balance of the cardiovascular system.

In one embodiment, the at least one wireless respiration sensor is further adapted to measure the respiratory signal of the user during said stress assessment.

According to another aspect, the present invention relates to a kit for stress management comprising:
a sensor assembly comprising:
at least one cardiac activity sensor for measuring the heart rate variability (HRV) signal of the user,
at least one respiration sensor for measuring the respiratory signal of the user,
a hand-held device (114, 115) comprising:
a receiver adapted to receive the measured signals,
a user interaction device,
a memory for storing the received signals, and
a processor adapted to:
assess the stress level of the user by determining a user related stress index, the stress index being used as an input in triggering commands instructing the output unit to provide the user with a messages indicating the stress level of the user,
monitor the user during a relaxation exercise by means of determining a relaxation index based on the measured HRV and respiratory signals by means of calculating an index of coherence between the HRV signal and the respiratory signal during the relaxation exercise, the relaxation index being continuously adapted to the incoming measured signals and based thereon the processor instructs the output unit to provide the user with biofeedback and support messages,
use the user specific data as an input in generating a first set of rules defining an improvement plan for self-management of stress and relaxation, said first set of rules being adapted to trigger commands instructing the output unit to provide the user with motivation related messages.

The aspects of the present invention may each be combined with any of the other aspects. These and other aspects of the invention will be apparent from and elucidated with reference to the embodiments described hereinafter.

BRIEF DESCRIPTION OF THE DRAWINGS

Embodiments of the invention will be described, by way of example only, with reference to the drawings, in which
FIG. 3 depicts a block diagram of a beginning phase of the system according to the present invention.

DESCRIPTION OF EMBODIMENTS

Figure 1:
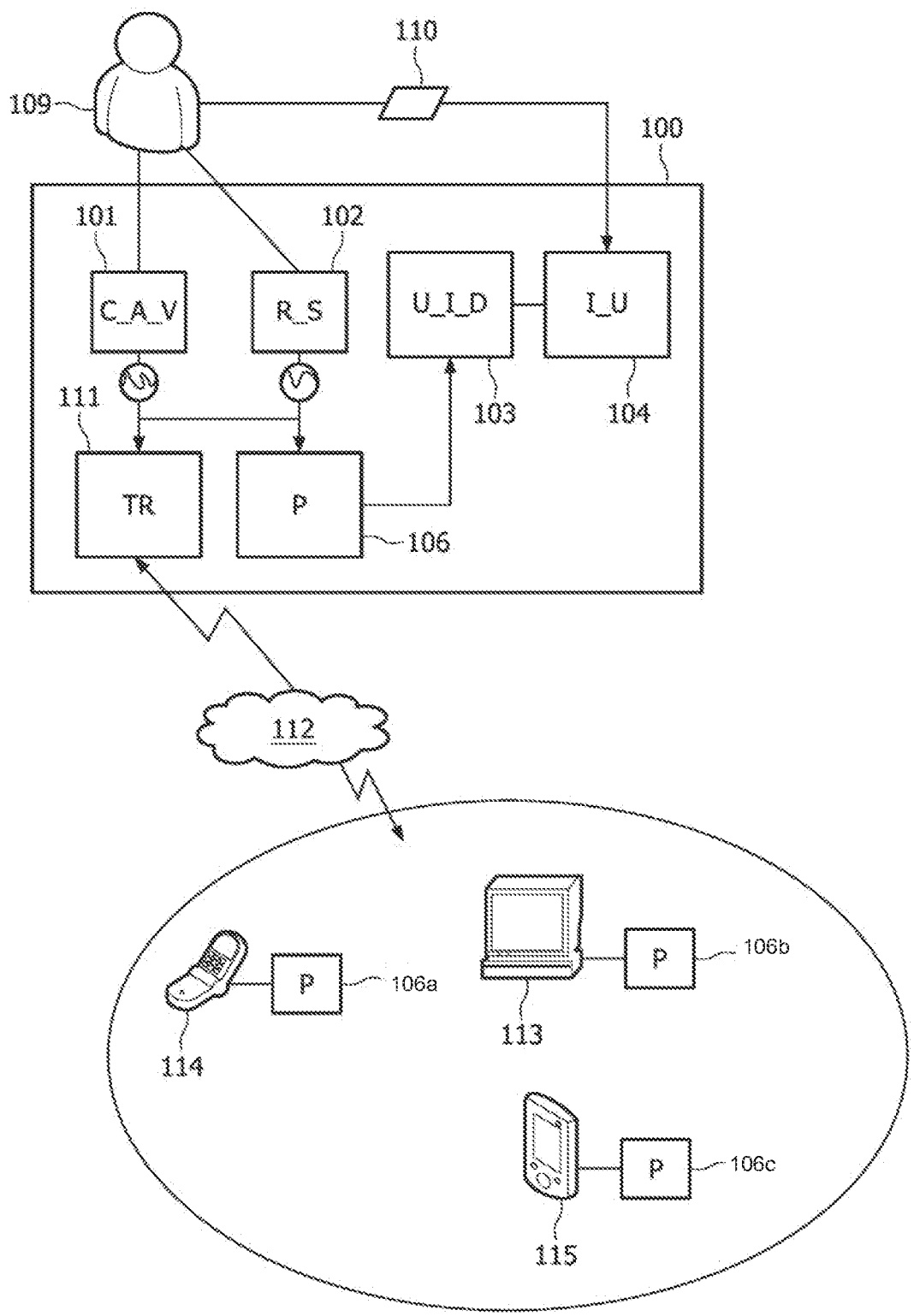
FIG. 1 shows a system according to the present invention for stress and relaxation management.

FIG. 1 shows a system 100 according to the present invention 1 for stress and relaxation management. The system comprises at least one cardiac activity sensor (C_A_V) 101, at least one respiration sensor (R_S) 102 adapted to be placed on a user 109 for measuring the heart rate variability (HRV) signal and the respiratory signal of the user respectively, a user interaction device (C_M) 103 and a processor (P) 106.

The user interaction device (U_I_D) 103 comprises an input unit (I_U) 104 for receiving user specific data and an output unit (not shown) for providing information output to the user. The user specific data may include data entered manually by the user, or data defining the user's profile via e.g. answering questionnaires 110 where the questionnaires may include questions relating to the gender of the user, whether the user is a smoker or non smoker, the weight, height, etc. of the user and the like. The questionnaires 110 may further be adapted to receive goal setting input data from the user indicating the personal goals the user aims to achieve, the goal setting input data being used in addition to said user's profile for determining long term action plan for the user.

The processor (P) 106 is adapted to assess the stress level of the user by determining a user related stress index. The stress index is used as an input in triggering commands instructing the output unit to provide the user with messages indicating the stress level of the user. Accordingly, such messages could as an example inform the user whether he/she should start with a relaxation exercise or not.

The processor (P) 106 is further adapted to monitor the user during a relaxation exercise by means of determining a relaxation index based on the measured HRV and respiratory signals by means of calculating an index of coherence between the HRV signal and the respiratory signal during the relaxation exercise. Preferably, the relaxation index is continuously adapted to the incoming measured signals and based thereon the processor instructs the output unit to provide the user with biofeedback and support messages.

The processor (P) 106 is further being adapted to use the user specific data as an input in generating a first set of rules defining an improvement plan for self-management of stress and relaxation. This first set of rules is adapted to trigger commands instructing the output unit to provide the user with motivation related messages.

In one embodiment, the stress level of the user is assessed by measuring the heart rate variability (HRV) signal of the user 109 while the user is initially in a first posture and moves towards at least a second posture where the measuring is continued. These first and second postures may be a lying (resting) and stand up postures. Accordingly, the measuring may be performed while the user is resting for e.g. few minutes, and while the user is standing for e.g. few minutes. It has been namely observed during active standing—a stimulus that physiologically enhances sympathetic activity—that a significantly smaller increase of normalized low frequency (LF) and a significantly smaller reduction of normalized high frequency (HF) occur in stressed patients compared to control ones. Such changes suggest a reduced responsiveness to excitatory stimuli during stress. HRV parameters may be analyzed in their variation and can be combined with standard information relative to the subject, such as age, gender, weight, smoke habits, blood pressure, etc. (see the embodiment here below), as well as the results of questionnaires. For the definition of the basic stress level, variations in the power spectral density of the HRV due to posture will be moreover evaluated and taken into account. Within a person's intra-individual variability range, the system can therefore provide stress assessment. An example of calculating said stress index is by, during said stress assessment, using a first HRV parameter associated to the first position and a second HRV parameter associated to the second position. Such HRV parameters may e.g. be obtained by studying the sequence of inter-beat intervals in time or frequency domain, where the HRV parameter may as an example be the power contained in certain frequency components estimated with spectral analysis, as described in "*European Heart Journal;* 1996; vol. 17, p. 358", hereby incorporated by reference. Other standard HRV measurements principle and HRV parameters may be implemented. The difference between HRV parameters is then used as an indicator to determine the user related stress index.

The at least one respiration sensor (R_S) 102 is, as mentioned previously, adapted to be placed on the user for measuring the respiratory signal of the user during the relaxation exercise. The respiration sensor (R_S) 102 may further be adapted to measure the respiratory signals of the user during said stress assessment.

In one embodiment, the cardiac activity sensor (C_A_V) 101 and the respiration sensor (R_S) 102 are wireless and unobtrusive and may be adapted to be integrated into textiles such as bra/vest/belt and the like.

In one embodiment, the processor (P) 106 is further adapted to compare the user related stress index, initially with baseline measures and subsequently with the previous determined stress indexes, wherein said comparing results in triggering commands instructing the output unit to provide the user with messages indicating the stress level of the user and trends. The baseline measures are typically determined during an initialization phase where the processor uses the measured signals to determine one or more of the following parameters:

a personal range for the stress index value, determined from said stress assessment, a personal range for the relaxation index value determined from said relaxation exercise, parameters which can be extracted from the cardiac activity and respiratory sensors, such as HRV parameters, breathing rate parameter, breathing amplitude parameter.

In one embodiment, the processor (P) 106 is further adapted to monitor the user's stress index over time by comparing with previous measured values. In case the stress index exhibits a negative trend, recommendations may be issued to assist the user 109 to reduce his stress level. The user is free to choose the frequency at which he would like to assess his stress, e.g. once every hour, once every day, once a week etc. Per default, it is recommended to measure the stress level at least once a week. The processor may further be adapted to monitor the user's compliance over time, the user's performance during relaxation exercise, and the user's progress over time.

In one embodiment, the processor (P) 106 is an external processor comprised in an external computer system 113, where the system 100 may thus communicate with the external computer system 113 via a communication channel 112 such as a wireless communication channel, e.g. Zigbee, blue tooth and the like, or via a wired connection. In this embodiment, the system 100 further comprises a transceiver (T) 111 for transmitting the measured signals to the external computer system 113 where said processing steps are performed. The external computer system 113 is thus adapted to transmit the stress index, the relaxation index and other calculations back to the system 100.

The processor (P) 106 may also be comprised in a hand-held device 114, 115 that is coupled to said sensors 101, 102, where the hand-held device can be a mobile phone 114, a PDA 115 and the like with e.g. a LCD screen as the output unit and the keyboard as the input unit (I_U) 104. Accordingly, the hand held device is coupled to the sensors 101, 102, either wired or wirelessly, for receiving and processing the measured signals as discussed previously and display said messages on the LCD screen.

Accordingly, the user 109 wearing such a hand-held device 114, 115 is provided with a personalized feedback about the stress index via e.g. the display on the hand-held device 114, 115 or via a voice command, based on relative comparisons with previous measurements. Also, the hand-held device 114, 115 provides the user with a coaching strategy to address the problems detected by monitoring and information derived from said questionnaires.

The hand-held device 114, 115 may be adapted to offer actively monitored relaxation exercises for lowering the overall stress level. Several studies, hereby incorporated by reference, have indeed demonstrated that relaxation exercises, e.g. based on regular and slower respiration, are significantly effective in lowering blood pressure, "*Treating hypertension with a device that slows and regularizes breathing: A randomized, double-blind controlled study*. Schein M, Gavish B, Herz M, Rosner-Kahana D, Naveh P, Knishkowy B, Zlotnikov E, Ben-Zvi N, Melmed RN. *Journal of Human Hypertension*; 2001, 15:271-278", "*Breathing-control lowers blood pressure*. Grossman E, Grossman A, Schein M H, Zimlichman R, Gavish B. *Journal of Human Hypertension*; 2001, 15:263-269", and hence in reducing risk factors for cardiovascular diseases (CVD). These exercises will according to the present invention be monitored and progress as well as compliance will be assessed. The system 100 or said hand-held device 114, 115 having integrated said features can support the user 109 with e.g. the following coaching measures:

Monitor the stress index and its trends as discussed previously, and provide the user 109 with recommendations for reducing the stress level and relaxation exercises will be proposed and reminded.

Monitor the activity level during daytime and if necessary suggest good times and ideas for doing exercises.

The system 100 or said hand-held device 114, 115 may in regular intervals test other factors influencing stress by means of a questionnaire.

In particular, a specific relaxation exercise may be monitored and coached by use of a real-time algorithm based on HRV analysis. The input signals are heart rate variability and respiratory activity computed on a beat-to-beat basis. They are obtained from the sensors integrated in a textile bra/vest. The algorithm calculates the coherence between HRV and respiration for the assessment of the current stress/relaxation level and displays the result on the hand-held device 114, 115. It is indeed well known that during a relaxed state, heartbeats and respiration are well synchronized.

In one embodiment, for biofeedback visualization on the user interface via the LCD screen on the hand-held device 114, 115, the biofeedback consists of two bars. One represents synchrony between HRV and respiration, which relates to a relaxed state and the other represents asynchrony between these two signals, which indicates a stressed state. The objective is thus to make the first bar as high as possible, e.g. by a slow and regular respiration rhythm, or equivalently to reduce the height of the second bar. Such an algorithm has been tested with a young, healthy user who first underwent a mental stress situation (examination) and after that performed a relaxation exercise. When this data set is used as an input signal to the algorithm, the stress bar is dominant during the first half of the recording whereas in the second half of the recording, the relaxation bar is dominant. Additionally, support will be provided with music. For a more sophisticated interface for biofeedback, the sound content, as well as the pictures, could be adjusted according to the detected stress/relaxation level and/or combined with a game. Hence, the user of the system gets information on his stress/relaxation level by means of graphical representations. This way it can be directly seen whether the user progresses on the way to a higher level of relaxation. Moreover, during the relaxation exercise, the user 109 gets direct feedback on the exercise's efficiency and quality and learns therefore how to better control his bodily functions. It should be noted that most of the existing devices propose a target pattern of optimized respiratory rhythm the user tries to match. However, if the user 109 does not adhere temporally to the breath indicator timing due to involuntary events, he has to interrupt momentarily the exercise to recover the rhythm, which breaks the positive effect of the relaxation exercise. This is however not the case in the proposed system 100 or device 114, 115, where the user 100 trains himself his respiratory activity.

As mentioned previously, the sensors used to obtain the HR, HRV, respiration frequency and amplitude may be integrated into textiles such as a vest or a. Additional embodiments include the measurement of parameters such as the skin temperature and the galvanic skin response, which are also shown to be correlated with stress, see "*Sympathetic nervous system activity in stress and biofeedback relaxation*. Shusterman V., Barnea O. *IEEE Engineering in Medicine and Biology Magazine*. March/April 2005", hereby incorporated by reference. The results may be calculated on the on-body electronics and sent via wireless technology to said portable or hand-held device 114, 115 for direct feedback and coaching. It should be noted that for the relaxation exercises, only the embodiment using the vest/bra is here explained, but other alternatives could be equally used. For example, the relaxation system could be integrated in a sofa/chair/bed or a car seat, e.g. the co-driver seat. Relaxation could hence be performed without wearing a special textile. Instead of a vest, a belt could also be used for measuring ECG and respiration, see "*Getting risk factors to goal: Lifestyle intervention is worth the effort in patients with hypertension, hyperlipidemia and/or hyperglycemia*. Gordon N F, Salmon R D, Saxon W E, et al. Paper presented at: 53rd annual scientific sessions of American College of Cardiology; Mar. 7-10, 2004; New Orleans", hereby incorporated by reference.

Embodiment of Various Sensors to be Used in the System According to the Present Invention:
Day Wear Bra/Vest (Shirt with Zipper):
Input Signals/Parameters:
  1-lead ECG from textile electrodes, positioned on the chest
  Respiration Signal from Piezo-Resistive Textile, Thoracic Position
Sample Rate:
  250 samples/sec for ECG
  25 samples/sec for respiration signal
Outputs/Results:
  HR, HRV
  Respiration frequency/amplitude
Accelerometer:
Input Signals/Parameters:
  3D-Accelerometer signals (e.g. integrated in on-body electronics)
Sample Rate:
  25 samples/sec
Output/Result:
  Activity index If the stress module is combined with a nightly monitoring, which might be recommended for long-term HR and HRV analysis, the following sensors are preferred to be integrated into the bed. Some of them deliver redundant information but could be combined to improve robustness and accuracy of the measurements.

Bed foil (e.g. an electret foil, see "*ElectroMechanical Film (EMFi)-A new multipurpose electret material*. Paajanen M, Lekkala J., Kirjavainen K., Sensors and Actuators A, Vol. 84. pp. 95-102, 2000", hereby incorporated by reference):
Input Signals/Parameters:
   Voltage caused by pressure/forces changes
   ~mV range
Position of Foil:
   According to the present status of our experiments, the best signal can be obtained when using a large area sensor (typically 300 by 600 mm2). It should be positioned in the thorax region, preferably ending slightly below the ribcage. Ideally, the foil can be integrated into the bed sheet, the mattress or the bedstead.
Sample Rate:
   Typical 250 samples/sec, can be up to 1 kHz. If HRV is not required can also be significantly lower
Output/Result:
   HR, HRV (based on heart mechanical activity) breathing rate, activity
Pillow and Foot Mat Electrode:
The pillow and the foot mat electrode will be used as sensors for HR and HRV estimation during night if the signal quality from the bed foil is not sufficient. The pillow and the foot mat electrode are composed of conductive woven yarn.
Input Signals/Parameters:
   Voltage signal from pillow and foot mat electrode
Electrode Positions:
   A large electrode in the foot area, another large area electrode in the head area
Sample Rate:
   250 samples/sec
Output/Result:
   HR, HRV (based on heart electrical activity)
Bed Post:
Input Signals/Parameters:
   Voltage caused by changes in weight distribution
Positions of Bed Post Sensors:
   Integrated in bed posts or in the bed frame
Sample Rate:
   Typical 250 samples/sec
Output/Result:
   HR, HRV (based on heart mechanical activity), breathing rate, activity
Slat Sensor:
Input Signals/Parameters:
   Strain in slat sensor sensed by strained gages (with bridge circuit)
Positions:
   Integrated in bed or sofa/chair
Sample Rate:
   250 Hz or lower
Output/Result:
   HR, HRV, breathing, activity
   The electronics provides various channels (one for each sensor) for data acquisition. For the two considered applications—day monitoring for relaxation exercises and night monitoring—two separate electronics are used. The electronics does typically not require user interface, but detect when the user puts on the wearable or enters the bed. The measurements are hence automatically started and stopped.
Embodiment of the Electronics to be Used in the System/Hand-Held Device:
On-Body Electronics for Vest:
Input Signals: ECG, respiration, activity accelerometer (part of on-body electronics)
Signal Processing:
   Lead-on detection (auto-on)
   Lead-off detection (auto-off)
   Signal quality check
   HR, HRV
   Respiration (rate, amplitude)
   Activity level
Power Supply:
   Battery: rechargeable
   Battery lifetime: 7 days (without Bluetooth)
Recharging Mechanism: Plugged External Charger or Contactless Charging
Memory
   Typically store raw data of 5 last sessions. (storage of raw data is optional. Raw data might be of interest for coaching by professionals)
Communication:
   Wired link to sensors
   Wireless communication with user interaction device
   Automatic connect
   Automatic download
   Automatic on/off
   Data Format: Binary data format
Form Factor:
   Size: as much as feasible miniaturization. Height<2 cm
Packaging:
   Water resistant, soft package
Stationary Electronics for Bed Sensors:
Input Signals: bed foil, pillow and foot mat electrode (Textile ECG)
Output Signals:
   Heart rate (from ECG and foil), HRV
   Respiration (rate, amplitude, from foil)
   Activity level (from foil)
   Signal quality check
Memory:
   Store output signals of last 5 sessions
Communication:
   Wired link to sensors
   Wireless communication with Patient Device
   Automatic connect
   Automatic download
   Automatic on/off (e.g. triggered by UI device)
Form Factor:
   Standard housing. The electronics is placed under the bed
Power Supply:
   Mains, batteries (rechargeable).
Embodiment of a User Interaction Device Requirements for Said System/Hand-Held Device:
   For the user interaction (information, feedback and coaching), a portable device with large LCD screen is required. The level of processing power, storage and display resources must allow to run the stress management module, but also other risk management modules. The user interaction device will provide a touch-screen or button menus to develop an intuitive user interface and to allow the evaluation of the applied coaching, motivation and feedback strategies. The device has to provide Bluetooth and LAN for communication and the following features for feedback display:
   Text format
   Graphics
   Optional is that it is further color coded
   Optional is that it is further an audio
   Optional is that it is further a video
   Optional is that it includes further a speech
   Active user input is required for example to fill in questionnaires about the subjective evaluation of the user's stress.

Use should be simple, which means that a variety of standard actions should be addressable in a one-button manner.
Embodiment of a User Interaction Device/Hand-Held Device:
General/Basic Components:
Processor AMD Alchemy AU1200 running at 500 MHz
 Xilinx Spartan-3 FPGA
Memory DDRAM: 128 Mbytes
 Flash: 64 Mbytes
Storage 40, 80 or 120 GBytes of hard disk storage. No system files on HDD.
Screen 3.7 inch high quality color LCD screen. 640*480*RGB pixels.
 Adjustable brightness.
Remote control: RC5 receiver
 7 function remote control included
Battery Replaceable high quality rechargeable Li-Ion battery (2200 mAh).
 Dimensions 145×107×38 mm
Weight 420 g
Upgrades Firmware fully user upgradeable.
Interfaces:
Memory cards: Supports CompactFlash (CF) cards, Type I/II and Microdrives.
 Other media (SmartMedia, Memory Stick, SD, MMC, xD) supported through optional adapter).
Interfaces:
upper: USB 2.0 high speed interface. The xSilo is recognized as a computer's external HDD, for fast up- and downloading from or to PC.
lower: USB 2 high speed OTG interface for connection to cameras and PictBridge enabled printers.
 WiFi enabled (the WiFi (IEEE802.11b) CompactFlash card is sold as an option).
 Extension connector: Ethernet
  2 JTAG connections (AMD and FPGA)
  Serial I/O
  DVI
Analog video out: PAL/NTSC selectable.
Analog audio out: Headphone/audio line out compatible.
 Built in loudspeaker with volume control.
Digital video out: High quality digital video out for connecting to LCD or plasma TVs and PC monitors.
Music:
Supported file formats MP3 files
Device functions Play, Stop, Fast Forward, Rewind
Movies:
Supported file formats On built-in LCD and external TV screens:
MPEG2 640*480 pixels-up to 10 Mbps-30 frames per second+audio 128 kbps
MPEG4 640*480 pixels-up to 4 Mbps-30 frames per second+audio 128 kbps
Device functions Play, Stop, Fast Forward, Rewind
Data Transmission Requirements:
 Data received from sensors in batches:
 Automatic connection and transmission
 by performing vital body signs measurement.
 by putting on the sensors (to ensure correct sensor placement).
 Data transmission to server on demand via E-mail/Internet.
 Trends and history of measurements are stored locally.
 Means for backup
Application Requirements:
 Simple to use
 Visualizations of long-term and short-term results.

Figure 2:
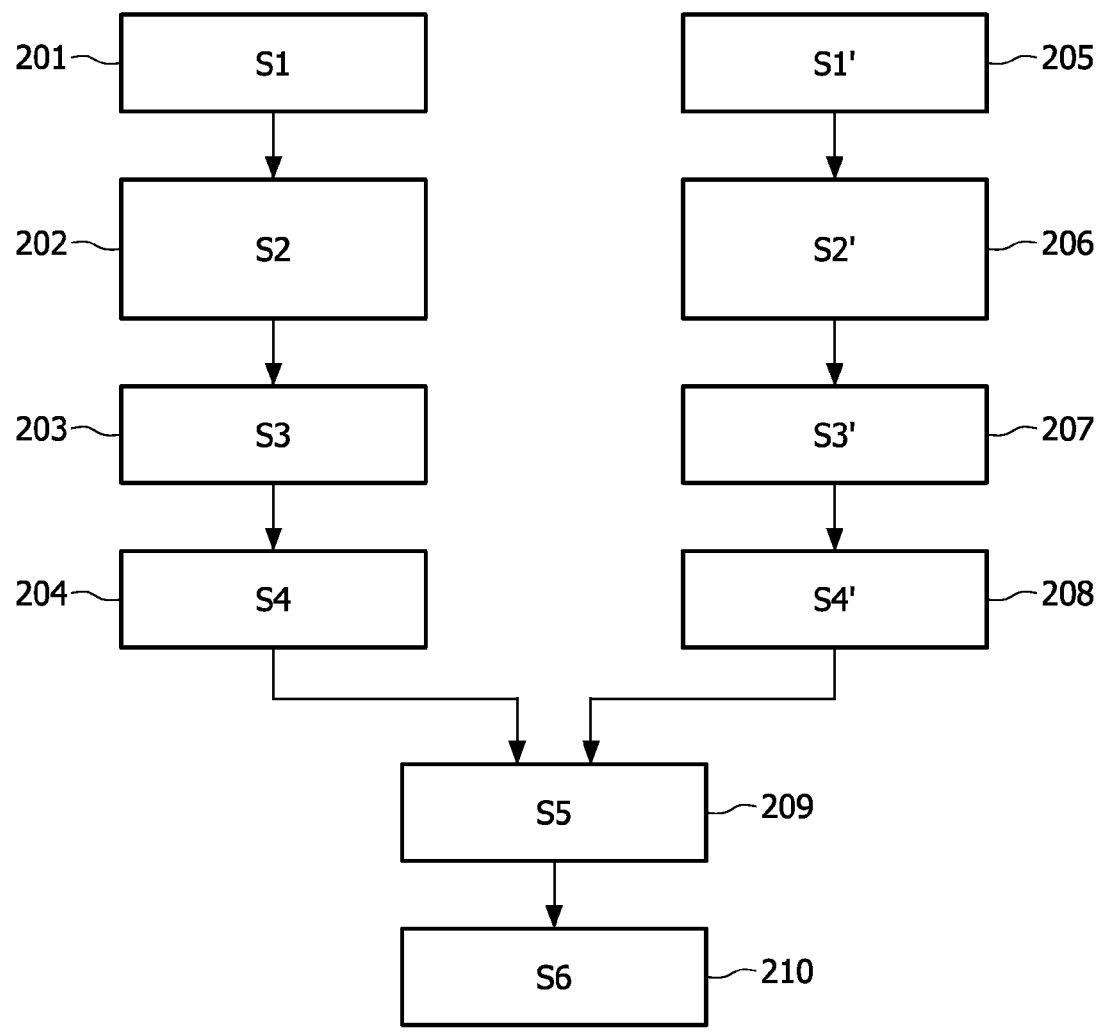
FIG. 2 depicts graphically a flowchart of the algorithm for relaxation.

Embodiment of a Personalized Algorithm:
The software used for extracting information from the signals that can be fed back to the user is an important feature. In this embodiment, two main algorithms can be distinguished:
Stress Assessment Procedure:
The algorithm provides a personalized stress index, based on frequency parameters derived from heart rate variability signal estimated during the measurement protocol (e.g. rest/stand) on a beat-to-beat basis, standard information relative to the user (such as age, gender, weight, smoking habits, blood pressure, etc.) and outputs of questionnaire. For example, the Subjective Stress-related Somatic Symptoms Questionnaire (4S-Q) could be used. It has shown to be significantly correlated with stress perception scale, see *Impact of Chronic Psychosocial Stress on Autonomic Cardiovascular Regulation in Otherwise Healthy Subjects*. Lucini D, Di Fede G, Parati G, Pagani M *Hypertension* 2005; 46; 1201-1206, hereby incorporated by reference.
Relaxation Exercise:
The sequence of analysis for the relaxation exercise, whose principle has been previously explained, is depicted in FIG. 2. In a first step (S1) 201 a raw ECG is measured from e.g. bra/vest, then a preprocessing (S2) 202 is performed, e.g. filtering, motion artifact detection, in a third step a R-peak detection is performed (S3) 203. A HRV analysis is then performed from the tachogram (S4) 204.
Parallel to this, the raw respiratory signal is measured from e.g. bra/vest, (S1') 205, then a preprocessing (S2') 206 is performed, e.g. filtering, motion artifact detection, a breathing cycle detection is performed (S3') 207, and the respirogram is then determined (S4') 208.
The results form these two parallel steps are then used as input for estimation of the coherence (S5) 209. The final result is then a real-time interface for biofeedback (S6) 210.
Embodiment of a User Feedback and Coaching:
Coaching and motivation strategies are used to support the customer in lowering his stress level, for example by learning relaxation techniques. The relaxation exercises are performed with direct biofeedback to teach the user how to relax in an optimal way. The stress management module offers two types of stress applications: coping with stress in daily life by relaxing e.g. at home and relaxation exercises as a help to fall asleep. This fall-asleep aid will contribute to the motivation and coaching in the sleep management module, as it will increase the sleep quality.
FIG. 3 depicts a block diagram of a beginning phase of the system according to the present invention. There will be checks on the actual status of the user; problem areas will be defined and improvement programs will be proposed. Goals will be set according to the individual preferences of the user. For example goals may be oriented towards improved performance or oriented towards changes in behavior. Daily assignments will be made and can be controlled, e.g. by questionnaires or by the monitoring unit. Furthermore, the goal setting takes into account the actual behavior of the user. A user exhibiting a sedentary lifestyle may be advised to practice some sport for relaxing and hence reducing his stress, while for the same purpose an active sportsman may be advised to relax by yoga.
The attractiveness of the improvement program lies to a large extent in the active involvement of the user to define goals and also in the selection of a suitable motivating strategy. This will be different for different types of users, who have been described in different psychological studies, e.g. as disclosed in "*Action phases and mind-sets*. Gollwitzer, P. M. In E. T. Higgins & R. M. Sorrentino (Eds.), *The handbook of* motivation and cognition: foundations of social behavior (Vol. 2, pp. 53-92) New York, Guilford Press", hereby incorporated by reference.

This strategy also implies that the parameters used to optimize the improvement program should be checked on different time scales. For example there are fixed parameters like user name, birthday and so on. Certain preferences or environmental factors vary slowly (e.g. a subjective evaluation of the work stress or family situation should be given approximately every month). Other parameters should be measured or evaluated daily—as long as the user does not feel annoyed by it.

Figure 4:
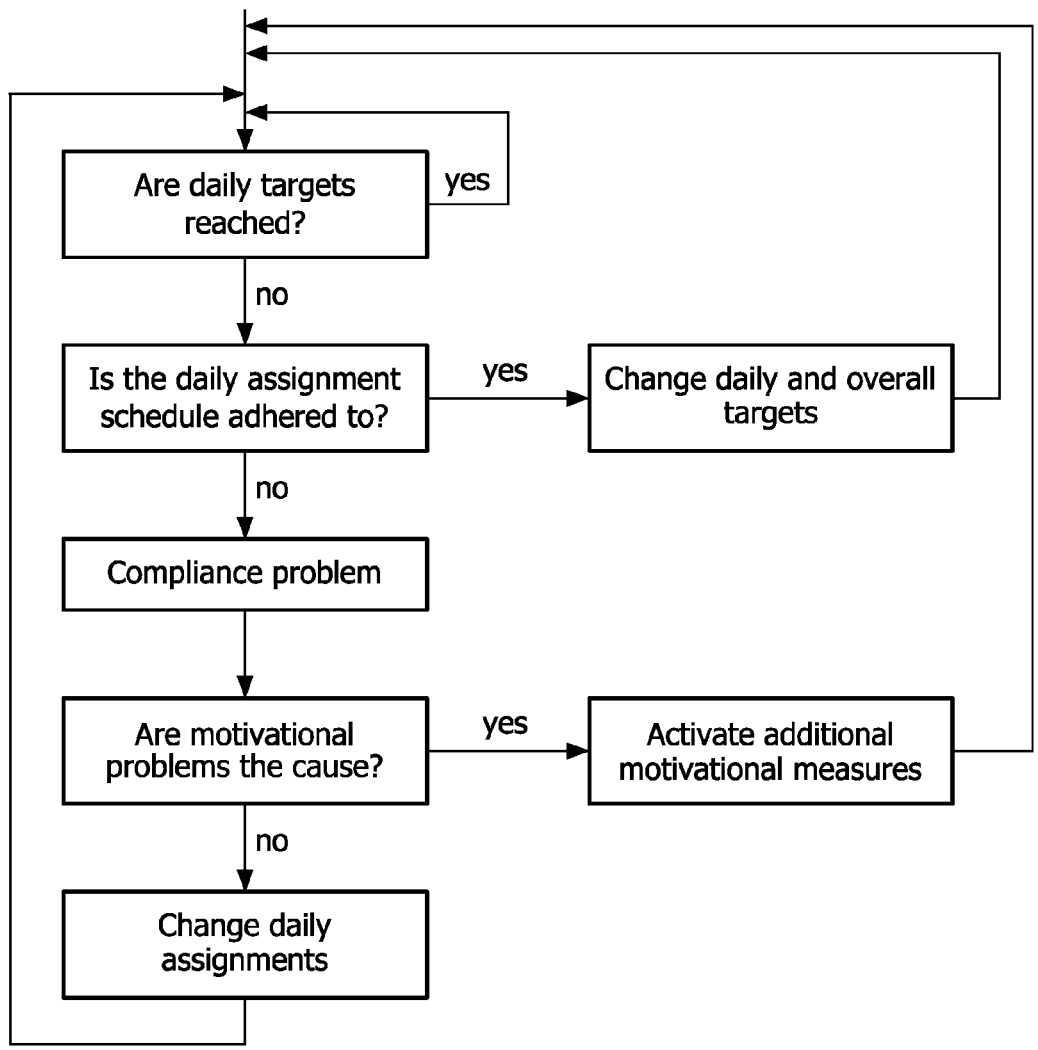
FIG. 4 shows a flowchart of a compliance check of the user.

FIG. 4 shows a flowchart of a compliance check of the user, which is another parameter that will be continuously monitored. If compliance goes down, countermeasures can be taken, in form of changing motivational patterns, asking for additional feedback, or stopping certain programs. As a fall back scenario human interaction via call centre should be taken into account. The system offers the option that the customer can send the data (stress index, trends) to a medical call centre to get personal advice by professionals.

Certain specific details of the disclosed embodiment are set forth for purposes of explanation rather than limitation, so as to provide a clear and thorough understanding of the present invention. However, it should be understood by those skilled in this art, that the present invention might be practiced in other embodiments that do not conform exactly to the details set forth herein, without departing significantly from the spirit and scope of this disclosure. Further, in this context, and for the purposes of brevity and clarity, detailed descriptions of well-known apparatuses, circuits and methodologies have been omitted so as to avoid unnecessary detail and possible confusion.

Reference signs are included in the claims, however the inclusion of the reference signs is only for clarity reasons and should not be construed as limiting the scope of the claims.

The invention claimed is:

1. A system for stress and relaxation management, comprising:
    at least one cardiac activity sensor for measuring a heart rate variability (HRV) signal of a user,
    at least one respiration sensor for measuring a respiratory signal the user (109),
    a user interaction device comprising an input unit for receiving user specific data and an output unit for providing information output to the user, and
    a processor adapted to assess the stress level of the user by determining a user related stress index, the user related stress index being determined based on a first and a second HRV parameter value associated with a first posture and a second posture, respectively, where a difference between the HRV parameter values is used as an indicator to determine the user related stress index, the stress index being used as an input in triggering commands instructing the output unit to provide the user with a message indicating the stress level of the user,
    the processor further being adapted to monitor the user during a relaxation exercise by means of determining a relaxation index based on the measured HRV and respiratory signals by means of calculating an index of coherence between the HRV signal and the respiratory signal during the relaxation exercise, the relaxation index being continuously adapted to the incoming measured signals and based thereon the processor instructs the output unit to provide the user with biofeedback and support messages,
    the processor further being adapted to use the user specific data as an input in generating a first set of rules defining an improvement plan for self-management of stress and relaxation, said first set of rules being adapted to trigger commands instructing the output unit to provide the user with motivation related messages.

2. A system according to claim 1, wherein said user specific data comprises at least one of:
    input data entered by the user via said input unit,
    input data obtained from the user via a response to questionnaires presented to the user,
    input data from an external agent communicating via said input unit, and
    data obtained from measured signals from said sensors.

3. A system according to claim 2, wherein at least a portion of said user specific data is further used to define a second set of rules indicating the user's personal goals.

4. A system according to claim 1, wherein said processor is further adapted to compare the user related stress index, initially with baseline measures and subsequently with previous determined stress indexes, wherein said comparing results in triggering commands instructing the output unit to provide the user with messages indicating the stress level of the user and trends.

5. A system according to claim 4, wherein said baseline measures are determined during a initialization phase where the processor uses the measured signals to determine one or more of the following parameters:
    a personal range for the stress index value, determined from said stress assessment,
    a personal range for the relaxation index value determined from said relaxation exercise,
    parameters which can be extracted from the cardiac activity and respiratory sensors, including one or more of the following:
    HRV parameters,
    breathing rate parameter,
    breathing amplitude parameter.

6. A system according to claim 1, wherein said user specific data comprises at least one of:
    input data entered by the user via said input unit,
    input data obtained from the user via a response to questionnaires presented to the user,
    input data from an external agent communicating via said input unit, and
    data obtained from measured signals from said sensors,
    wherein said comparing with the previous determined stress indexes further includes comparing the stress index with the second set of rules indicating the user's personal goals and adapting the second set of rules to the outcome of the comparing with the second set of rules.

7. A system according to claim 1, wherein the processor is further adapted to determine at least one of the following parameters:
    trend and progress related parameter indicating trends and progress of the user, where the determining is based on one or more of the following:
    comparing said indexes with previous indexes,
    comparing said indexes with said second set of rules,
    comparing said indexes with previous indexes and said second set of rules,
    performance related parameter indicating the performance of the user during the relaxation exercise, said determining being based on comparing the determined relaxation index with previously determined relations indexes, and
    compliance related parameter indicating the compliance of the user to follow said second set of rules, said determining being based on the monitoring of determined indexes and said current set of second set of rules, wherein the processor is further adapted to adapt the first set of rules to one or more of said parameters.

8. A system according to claim 3, wherein prior to defining said second set of rules, proposal rules are presented to the user via said output unit, where in case the user agrees on the proposal rules via said input unit, said processor issues a command triggering said proposal rules to become said second set of rules.

9. A system according to claim 3, wherein the second set of rules is used as input in defining said first set of rules.

10. A system according to claim 4, wherein said comparing of the user related stress index with the baseline measures and subsequently with the previous determined stress indexes further includes means of comparing the subsequent stress indexes with the previous determined stress indexes along with said second set of rules indicating the user's personal goals.

11. A system according to claim 1, wherein the at least one cardiac activity and respiration sensors are wireless and unobtrusive.

12. A system according to claim 11, wherein said at least one cardiac activity and respiration sensors are integrated into textiles.

13. A system according to claim 1, further comprising at least one of:
- a temperature sensor adapted to measure the temperature of the skin of the user,
- a galvanic skin response sensor adapted to measure the galvanic skin response,
- a pillow electrode integrated into a pillow, combined with a foot mat electrode integrated into a bed sheet, for measuring heart rate (HR) and HRV signals,
- bed post sensor adapted to be integrated or mounted to a bed frame or measuring HR or HRV or both HR and HRV signals,
- a slat sensor or a foil sensor adapted to be integrated into a bed or a sofa or a chair for measuring at least one of the following:
HR signal,
HRV signal,
the respiration of the user,
the activity of the user.

14. A system according to claim 1, wherein the processor is an external processor incorporated into one of: an external computer system and a hand-held device, the system further comprising a transceiver for transmitting the measured signals to the external computer system or the hand-held device where said processing steps are performed.

15. A system according to claim 1, wherein the system further comprises a transceiver, the processor (106), the user interaction device and the transceiver being integrated into a hand-held device.

16. A system according to claim 1, wherein the first posture is a rest posture and the second posture is a stand-up posture.

17. A system according to claim 1, wherein the at least one wireless respiration sensor is further adapted to measure the respiratory signal of the user during said stress assessment.

* * * * *